United States Patent [19]

Diana

[11] 4,052,382
[45] Oct. 4, 1977

[54] 1-PHENYL-3-AZACARBOCYCLIC-UREAS

[75] Inventor: Guy D. Diana, Stephentown, N.Y.

[73] Assignee: Sterling Drug Inc., New York, N.Y.

[21] Appl. No.: 633,444

[22] Filed: Nov. 19, 1975

Related U.S. Application Data

[60] Division of Ser. No. 536,755, Dec. 27, 1974, Pat. No. 3,963,748, which is a continuation-in-part of Ser. No. 266,695, June 27, 1972, abandoned, which is a division of Ser. No. 82,799, Oct. 21, 1970, Pat. No. 3,717,648, which is a continuation-in-part of Ser. No. 733,323, May 31, 1968, abandoned.

[51] Int. Cl.$^2$ .................. C07D 207/22; C07D 211/72; C07D 233/04
[52] U.S. Cl. .................. 260/239 BE; 260/239 BF

[58] Field of Search .................. 260/239 BE, 239 BF

[56] References Cited

U.S. PATENT DOCUMENTS 3,717,648  2/1973  Diana .................. 260/239 BE

Primary Examiner—Raymond V. Rush
Attorney, Agent, or Firm—Frederik W. Stonner; B. Woodrow Wyatt

[57] ABSTRACT

The compounds of this invention are 1-phenyl-3-azacarbocyclic-ureas having anthelmintic activity which are prepared by the reaction of azacarbocyclicamines or azacarbocyclicimines with appropriate phenyl isocyanates.

2 Claims, No Drawings

1-PHENYL-3-AZACARBOCYCLIC-UREAS

This application is a division of application Ser. No. 536,755, filed Dec. 27, 1974, now U.S. Pat. No. 3,963,748, issued June 15, 1976, which in turn is a continuation-in-part of application Ser. No. 266,695, filed June 27, 1972, now abandoned, which in turn is a division of application Ser. No. 82,799, filed Oct. 21, 1970, now U.S. Pat. No. 3,717,648, issued Feb. 20, 1973, in turn a continuation-in-part of application Ser. No. 733,323, filed May 31, 1968, now abandoned.

This invention relates to novel 1-phenyl-3-azacarbocyclic-ureas and to intermediates therefor.

In one aspect of this invention, there is provided novel 1-phenyl-3-azacarbocyclic-ureas of the formula

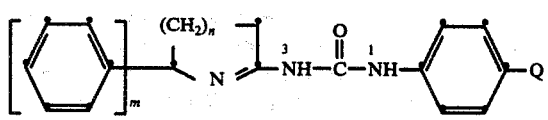

I where when $n$ is the integer 1 and $m$ is zero then Q is chlorine or bromine; when $n$ is the integer 2 and $m$ is zero then Q is hydrogen or chlorine; when $n$ is the is the integer 2 and $m$ is the integer 1 then Q is chorine; and when $n$ is the integer 3 and $m$ is zero then Q is chlorine.

Another aspect of this invention provides novel 1-phenyl-3-(1-phenylpyrrolidinylene)ureas having the formula

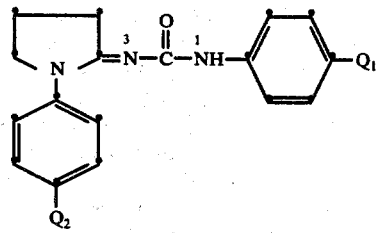

II where $Q_1$ and $Q_2$ are halo.

The compounds of formula I and formula II are useful as anthelmintic agents.

The 1-phenyl-3-azacarbocyclic-ureas of formula I exist in tautomeric forms as illustrated by the formulas

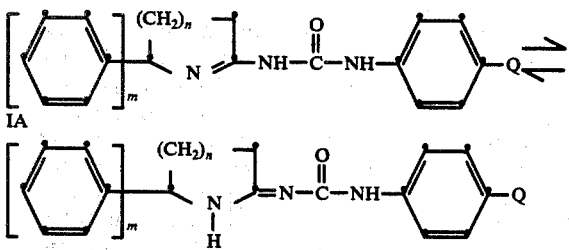

I

IA

As with all tautomeric systems, the rate of transformation I ⇌ IA and the ratio I/IA are dependent on the thermodynamic environment, including the state of aggregation, so that results of measurements by any particular technique do not necessarily have relevance except under the conditions of the measurement, thereby, among other consequences, giving rise to problems for any simple designation of the physical embodiments. Thus, measurement of the infrared spectra in potassium bromide admixture and measurement of the nuclear magnetic resonance spectra are not helpful in determining which tautomeric form, I or IA is present or predominates in any given state of aggregation or solution and therefore the names based on structure I are preferred although it is understood that either or both structures I and IA are comprehended.

The compounds of formula I are prepared by reacting, in a suitable solvent, that is, a solvent which is essentially inert under the conditions of the reaction, an azacarbocyclicamine of the formula

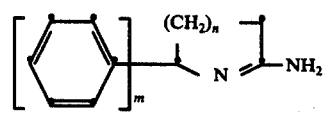

III with a 4-Q-phenyl isocyanate.

The exothermic reaction is carried out by reacting the intermediate compound of formula III with a 4-Q-phenyl isocyanate in an inert solvent, e.g., benzene, acetone or chloroform at temperatures ranging from 0° C. to the reflux temperature of the reaction mixture, for a period of about 2 to 24 hours.

The reaction is preferably carried out by reacting the intermediate compound of formula III with about one equivalent of a 4-Q-phenyl isocyanate at temperatures ranging from about 0° C. to room temperature for a period of about 16 hours.

The compounds of formula II are prepared by reacting a 2-imino-1-phenylpyrrolidine of the formula

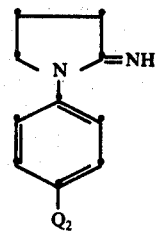

IV with a 4-$Q_1$-phenyl isocyanate using the process described hereinabove for the preparation of the compounds of formula I.

The azacarbocyclicamine of formula III and the 2-imino-1-phenylpyrrolidine of formula IV, in the free base form, employed as a starting material in the above-described process, is prepared from the corresponding salt, e.g., the hydrochloride, by reacting such salt with a stoichiometric amount of an appropriate base in a suitable solvent, for example, sodium acetonide in acetone, triethylamine in chloroform, or sodium methoxide in benzene. It is preferred to use the resulting solution of the amine or imine directly in the next step but the amine or imine can be isolated by conventional techniques before use.

The intermediate compound of formula III in its acid-addition salt form is prepared by reaction of a cyclic imino ether of the formula

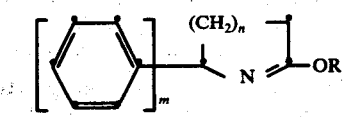

where R is lower-alkyl, with an ammonium salt, for example, ammonium chloride. The reaction is carried out in a suitable solvent, e.g. methyl or ethyl alcohol, at room temperature.

The intermediate cyclic imino ether of formula V can be readily prepared by well-known methods, that is, by the reaction of a lactam of the formula

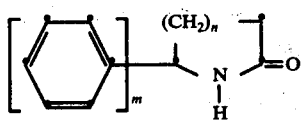

VI with a lower-alkyl alcohol, e.g., methyl or ethyl alcohol, in the presence of a catalytic amount of an acid, e.g., hydrochloric acid; or with a lower-alkyl orthoformate, e.g., ethyl or methyl orthoformate, in the presence of a catalytic amount of an acid, e.g. hydrochloric acid or p-toluenesulfonic acid. A preferred intermediate cyclic imino ether is the cyclic imino ethyl ether which is prepared by yet another well-known method, e.g., by reacting a compound of formula VI, in a suitable solvent, e.g. methylene dichloride, with triethyloxonium fluoroborate which can be readily prepared by a known process, that is, by treating boron trifluoride-etherate in ether with epichlorohydrin.

The intermediate lactam of formula IV, where $m$ is the integer 1 and $n$ is the integer 2, is prepared by reacting 4-benzoylbutyric acid, a known compound, with ammonium carbonate-formic acid at elevated temperatures, e.g., about 150°–200° C., for about 24 hours.

The intermediate lactams represented by formula VI where $n$ is the integer from 1 to 3 and $m$ is the integer 0 are readily available compounds that are well-known in the art.

The intermediate 4-Q (and 4-$Q_1$)-phenyl isocyanates belong to well-known class of compounds and can be readily prepared by conventional methods, for example, by condensing a 4-Q-aniline or 4-$Q_1$-aniline with one equivalent of phosgene in a suitable solvent, for example toluene, and heating or distilling the resulting carbamyl chloride whereupon hydrogen chloride is eliminated. The resulting corresponding isocyanate can be isolated and purified by standard techniques.

Other well-known procedures that can be used for the preparation of the 4-Q (and 4-$Q_1$)-phenyl isocyanate are the Hoffmann, Curtius, or Lossen rearrangements of an appropriate amide, acid azide, or hydroxamic acid respectively obtained by well-known procedures from the corresponding known 4-Q (and 4-$Q_1$)-benzoic acids.

The intermediate compound of formula IV in its acid addition salt form can be prepared by the reaction of a 4-halobutyronitrile with at least an equivalent of a 4-$Q_2$-aniline or a 4-$Q_2$-N-methylaniline, either of which can be used to give the identical corresponding compound of formula IV, but it is preferred to use 4-$Q_2$-N-methylaniline.

The exothermic reaction is generally carried out by heating about equivalent amounts of the reactants at a temperature ranging from about 200° C. to about 300° C. for from about one-half hour to about ten hours; if desired the reaction can be carried out in a suitable inert solvent.

The intermediate 4-$Q_2$-anilines and 4-$Q_2$-N-methylanilines belong to a well-known class of compounds. The 4-$Q_2$-N-methylanilines are readily prepared from the corresponding 4-$Q_2$-anilines by known methods, that is, by reacting the latter with methyl orthoformate and hydrolysis of the corresponding N-methylformamide with sulfuric acid.

The intermediate 4-halobutyronitriles are readily available compounds well-known in the art.

As used throughout this specification the term "halo" includes chloro, bromo, fluoro, and iodo.

The novel compounds of the instant invention are the compounds of formula I and formula II and the acid-addition salts thereof. The compounds of formula I and formula II in free base form are converted to the acid-addition salt form by interaction of the base with an acid. In like manner, the free bases can be regenerated from the acid-addition salt form in the conventional manner, that is by treating the salts with strong aqueous bases, for example alkali metal hydroxides, alkali metal carbonates, and alkali metal bicarbonates. The bases thus regenerated can then be interacted with the same or a different acid to give back the same or a different acid-addition salt. Thus the novel bases and all of their acid-addition salts are readily interconvertible and are the full equivalents of each other.

It will thus be appreciated that formula I and formula II not only represent the structural configuration of the bases of formula I and formula II respectively, but are also representative of the structural entity which is common to all of my compounds of formula I and formula II respectively, whether in the form of the free bases or in the form of the acid-addition salts of the bases. I have found that by virtue of this common structural entity, the bases of formula I and formula II and their acid-addition salts have inherent pharmacodynamic activity of a type more fully described hereinbelow. This inherent pharmacodynamic activity can be enjoyed in useful form for pharmaceutical purposes by employing the free bases themselves or the acid-addition salts formed from pharmaceutically-acceptable acids, that is, acids whose anions are innocuous to the animal organism in effective doses of the salts so that beneficial properties inherent in the common structural entity represented by the free bases are not vitiated by side-effects ascribable to the anions.

In utilizing this pharmacodynamic activity of the salts of the compounds of formula I and formula II, I prefer of course to use pharmaceutically acceptable salts. Although water-insolubility, high toxicity, or lack of crystalline character may make some particular salts species unsuitable or less desirable for use as such in a given pharmaceutical application, the water-insoluble or toxic salts can be converted to the corresponding pharmaceutically acceptable bases by decomposition of the salt with aqueous base as explained above, or alternatively, they can be converted to any desired pharmaceutically acceptable acid-addition salt by double decomposition reactions involving the anion, for example, by ion-exchange procedures.

Moreover, apart from their usefulness in pharmaceutical applications, the salts of the compounds of formula I and formula II are useful as characterizing or identifying derivatives of the corresponding free bases or in isolation or purification procedures. Like all of the acid-addition salts, such characterizing or purification salt derivatives can, if desired, be used to regenerate the free bases by reaction of the salts with aqueous base, or alternatively can be converted to other acid-addition salts by, for example, ion-exchange procedures. Thus, by using such purification procedures the pharmaceutically acceptable free bases of the compounds of formula I and formula II, or alternatively their pharmacetically accepted acid-addition salts, can be prepared.

It will be appreciated from the foregoing that all of the acid-addition salts of my new bases are useful and valuable compounds, regardless of considerations of solubility, toxicity, physical form, and the like, and are accordingly within the purview of the instant invention.

The novel feature of the compounds of the invention, then resides in the concept of the bases and cationic forms of the new compounds of formula I and formula II and not in any particular acid moiety or acid anion associated with the salt forms of these compounds; rather, the acid moieties or anions which can be associated in the salt forms are in themselves neither novel nor critical and therefore can be any acid anion or acid-like stubstance capable of salt formation with bases. In fact, in aqueous solutions, the base form or water-soluble acid-addition salt form of the compounds of the invention both possess a common protonated cation or ammonium ion.

Thus the acid-addition salts discussed above and claimed herein are prepared from ay organic acid, inorganic acid (including organic acids having an inorganic group therein), or organo-metallic acid as exemplified by organic mono- and poly-carboxylic acids, such as found, for example, in Beilstein's Organische Chemie, 4th ed., Volumes III, IV, IX, X, XIV, XVII, XIX, XXI, XXII, and XXV; organic mono and polysulfonic and -sulfinic acids, such as found, for example, in Beilstein Volumes VI, XI, XVI, and XXII; organic phosphonic and phosphinic acids, such as found, for example, in Beilstein Volumes XI and XVI; organic acids of arsenic and antimony, such as found, for example, in Beilstein Volume XVI; organic heterocyclic carboxylic, sulfonic, and sulfinic acids, such as found, for example, in Beilstein Volumes XVIII, XXII, and XXV; acidic ion-exchange resins; and inorganic acids of any acid forming element or combination of elements, such as found in Mellor, Comprehensive Treatise on Inorganic and Theoretical Chemistry, Longman's, Green and Co., New York, N.Y., Volumes I-XVI. In addition, other salt-forming compounds which are acidic in their chemical properties but which are not generally considered as acids in the same sense as carboxylic or sulfonic acids are also considered to be among the numerous acids which can be used to prepare acid-addition salts of the compounds of the invention. Thus there is also comprehended acidic phenolic compounds, such as found, for example in Volume VI of Beilstein, acidic compounds having "activated" or acidic hydrogen atoms, as for example, picrolonic acid, or barbituric acid derivatives having an acidic proton, such as found, for example, in Cox et al., Medicinal Chemistry, Vol. IV, John Wiley and Sons, Inc. New York, N.Y. (1959). Also comprehended as salt-forming agents are so-called Lewis acids which lack a pair of electrons in the outer "electron shell" and react with basic compounds having an unshared pair of electrons to form sals, for example boron trifluoride.

Representative acids for the formation of the acid-addition salts include formic acid, acetic acid, trifluoroacetic acid, isobutyric acid, alph-mercaptopropionic acid, malic acid, furmaric acid, oxalic acid, succinic acid, succinamic acid, glutamic acid, tartaric acid, citric acid, pamoic acid, lactic acid, glycolic acid, gluconic acid, saccharic acid, ascorbic acid, penicillin, benzoic acid, 4-methoxybenzoic acid, phthalic acid, salicylic acid, acetylsalicylic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, pyromucic acid, cholic acid, pyrenecarboxylic acid, 2-pyridinecarboxylic acid, 3-indoleacetic acid, quinic acid, sulfamic acid, methanesulfonic acid, ethanesulfonic acid, benzenesulfinic acid, butylarsonic acid, diethylphosphinic acid, p-aminophenylarsinic acid, phenylstibnic acid, phenylphosphinous acid, methanephosphonic acid, phenylphosphinic acid, acidic resins, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride and the like. The acid-addition salts are prepared either by dissolving the free base in an aqueous solution containing the appropriate acid and isolating the salt by evaporating the solution, or by reacting the free base and acid in an organic solvent, in which case the salt separates directly or can be obtained by concentration of the solution.

The compounds of formula I and formula II of this invention have been tested in dogs by standard chemotherapeutic evaluation procedures described hereinbelow and were found to possess anthelmintic activity, in particular anti-hookwork activity and are useful as anthelmintic agents, in particular as anti-hookworm agents.

TEST PROCEDURE FOR THE DETERMINATION OF ANTHELMINTIC ACTIVITY

Anti-hookworm Activity: Both naturally infected and artificially infected mongrel dogs were used in the test. The naturally infected dogs carried a burden of two kinds of hookworm (Uncinaria stenocephala and Ancylostoma canium). The artificially infected dogs were treated with sufficient hookworm (Ancylostoma caninum) larvae approximately 1 month prior to treatment with a test agent to insure that a mature infection would be present at the time of the test. Food was withheld from the dogs for a minimum of 5 hours prior to, and for 3 to 5 hours after each, administration of the test agent. Equal doses of the test agent were administered orally to from two to three dogs, infected naturally or artificially, one or two doses per dog per day for from 1 to 5 consecutive days. The dogs were sacrificed 5 to 8 days post-first medication and the intestines were searched for worms.

The novel compounds of this invention were found to reduce or eliminate the hookworm burden from the infected dogs when administered in the dose range of from 25 to 125 mg./kg. (calculated on the basis of the free base). The number of doses administered ranged from one to two per day for from one to five consecutive days, depending on the severity of the helminth infection.

The actual determination of the numercial biological data definitive for a particular compound is readily determined by standard test procedures by technicians versed in pharmacological test procedures, without the need for any extensive experimentation.

The compounds of formula I and formula II can be incorporated in unit dosage form as tablets or capsules for oral administration either along or in combination with suitable adjuvants such as calcium carbonate, starch, lactose, talc, magnesium stearate, gum acacia, and the like. Still further the compounds can be formulated for oral administration in aqueous alcohol, glycol, or oil solutions or oil-water emulsions in the same manner as conventional medicinal substances are prepared. Furthermore, if it is desired to broaden the spectrum of activity and/or to secure the advantages of potentiated action, the formulations can have incorporated in them, in addition to the compounds of formula I and/or formula II, one or more other orally effective anthelmintic and/or potentiating agents. For example such agents, without limiting the generality of the foregoing, can be illustrated by piperazine in the case of ascariasis and enterobiasis; thiabendazole in the case of ascariasis, strongyloidiasis, trichuriasis and trichinosis; pyrvinium in the case of enterobiasis and strongyloidiasis; quinacrine, aspidium, bithionol and niclosamide in the case of tapeworm infections; bithionol in case of trematode infections and biphenium in the case of ascariasis and trichuriasis.

The molecular structures of the compounds of this invention were assigned on the basis of the method of their synthesis and study of their infrared spectra, and confirmed by the correspondence between calculated and found valves for the elementary analysis for respentative examples.

The following examples will further illustrate the invention without, however, limiting it thereto;

EXAMPLE 1

1-Phenyl-3-(3,4,5,6-tetrahydro-2-pyridyl)urea

To a mixture, prepared by reacting 5.03 g. sodium with 300 ml. dry acetone, was added 29.6 g. 2-iminopiperidine hydrochloride at room temperature and the mixture was stirred for 30 minutes. A solution of 26.1 g. phenyl isocyanate in 200 ml. dry acetone was added dropwise during 1 hour and stirring was continued for 18 hours. The mixture was filtered and the collected solids were slurried in water and collected by filtration. The acetone filtrate was concentrated to dryness under reduced pressure, the residue was treated with 500 ml. ether, and the resulting solid which separated was collected by filtration, combined with the solid obtained above from the water slurry, and recrystallized from isopropyl alcohol to give 30.4 g. 1-phenyl-3-(3,4,5,6-tetrahydro-2-pyridyl)urea; m.p. 153°–154° C.

EXAMPLE 2

1-(4-Chlorophenyl)-3-(3,4,5,6-tetrahydro-2-pyridyl)urea

To a mixture, prepared by reacting 0.9 g. sodium in 150 m. dry acetone, was added 5.36 g. 2-iminopiperidine hydrochloride at room temperature and the mixture was stirred for 30 minutes. A solution of 6.1 g. 4-chlorophenyl isocyanate in 20 ml. dry acetone was added dropwise during 1 hour, stirring was continued for 18 hours, and the mixture was evaporated to dryness under reduced pressure. A solution of the residue in ether was chilled, filtered and ethereal hydrogen chloride was added until acidic. The resulting solid was collected by filtration, washed with ether and recrystallized from ethyl alcohol to yield 5.5 g. of the hydrocholoride of 1-(4-chlorophenyl)-3-(3,4,5,6-tetrahydro-2-pyridyl)urea; m.p. 200°–203° C.

EXAMPLE 3

1-(4-Bromophenyl)-3-(1-pyrrolin-2-yl)urea

Following a procedure similar to that described in Example 2 but using 4.6 g. sodium in 300 ml. dry acetone, 23.2 g. 2-amino-1-pyrroline hydrochloride and 38.9 g. 4-bromophenyl isocyanate in 200 ml. dry acetone, there was obtained after recrystallization from ethyl alcohol 10.8 g. of the hydrochloride of 1-(4-bromophenyl)-3-(1-pyrrolin-2-yl)urea; m.p. 221°–224° C.

EXAMPLE 4

1-(4-Chlorophenyl)-3-(1-pyrrolin-2-yl)urea

Following a procedure similar to that described in Example 1 but using 15.3 g. sodium in 1900 ml. dry acetone, 80 g. 2-amino-1-pyrroline hydrochloride, and 102 g. 4-chlorophenyl isocyanate in 500 ml. dry acetone, except that ice-bath cooling was applied during the addition of the isocyanate, there was obtained after recrystallization from ethyl acetate 66 g. 1-(4-chlorophenyl)-3-(1-pyrrolin-2-yl)urea; m.p. 147°–150° C.

Treatment of a chilled solution of the free base in absolute alcohol with ethereal hydrogen chloride yielded after recrystallization from absolute ethyl alcohol the hydrochloride of 1-(4-chlorophenyl)-3-(1-pyrrolin-2-yl)urea; m.p. 217°–221° C.

EXAMPLE 5

1-(4-Chlorophenyl)-3-(3,4,5,6-tetrahydro-2H-azepin-7-yl)urea

A. Following a procedure similar to that described in Example 1 but using 3.71 g. sodium in 300 ml. dry acetone, 26.4 g. 7-amino-3,4,5,6-tetrahydro-2H-azepin hydrochloride and 27.3 g. 4-chlorophenyl isocyanate in 200 ml. ry acetone there was obtained after recrystallization from isopropyl alcohol 24 g. 1-(4-chlorophenyl)-3-(3,4,5,6-tetrahydro-2H-azepin-7-yl)urea; m.p. 142°–142.5° C.

B. The 7-amino-3,4,5,6-tetrahydro-2H-azepine hydrochloride used above was prepared as follows:

To a solution of 45.2 g. 7-ethoxy-3,4,5,6-tetrahydro-2H-azepin in 200 m. methyl alcohol was added 17.8 g. ammonium chloride at room temperature and the mixture was stirred for 2 hours. The resulting solution was allowed to stand at room temperature for 3 days and was then evaporated to dryness to yield after recrystallization from isopropyl alcohol 26.4 g. 7-amino-3,4,5,6-tetrahydro-2H-azepin hydrochloride; m.p. 160°–161° C.

C. The 7-ethoxy-3,4,5,6-tetrahydro-2H azepin used above was prepared as follows:

To a solution of 91 g. boron trifluoride-etherate in 300 ml. anhydrous ether was added 44.4 g. epichlorohydrin with stirring and at a rate which maintained gentle reflux. The mixture was stirred at room temperature for 2 hours and the supernatant ether was decanted from the solid triethyloxonium fluoroborate which as then washed several times with anhydrous ether and suspended in 50 ml. dry methylene dichloride. A solution of 45.2 g. hexahydro-2-azepinone in 300 ml. dry methylene dichloride was added dropwise and the solution was stirred at room temperature for 16 hours. A 50 percent aqueous potassium carbonate solution (76 g.) was added with stirring and the supernatant liquid was separated from the resulting solids by decantation and evaporated to dryness under reduced pressure. The resulting oil was distilled to give 45.2 g. 7-ethoxy-3,4,5,6-tetrahydro-2H-azepine; b.p. 76°-77° C. (23 mm.); $n^{25}D$ 1.4535.

EXAMPLE 6

1-(4-Chlorophenyl)-3-[1-(4-chlorophenyl)-2-pyrrolidinylene]urea

A. To a stirred solution of 15 g. 2-imino-1-(4-chlorophenyl)-pyrrolidine hydrochloride in 200 ml. chloroform was added 6.6 g. triethylamine, stirring was continued several minutes and a solution of 9.97 g. 4-chlorophenyl isocyanate in 50 ml. chloroform was added dropwise. The solution was allowed to stand at room temperature for 16 hours and was then washed with water and dried over sodium sulfate. The chloroform was evaporated under reduced pressure to give after recrystallization from ethyl alcohol 15.4 g. 1-(4-chlorophenyl)-3-[1-(4-chlorophenyl)-2-pyrrolidinylene]urea; m.p. 177°-178° C.

B. The 2-imino-1-(4-chlorophenyl)pyrrolidine hydrochloride used above was prepared as follows:

The temperature of a solution of 9:10 g. 4-chloro-N-methylaniline and 6.63 g. 4-chlorobutyronitrile was increased until gas evolution was noted (200° C.) and the bath temperature was maintained at 205°-210° C. until the gas evolution subsided (45 minutes). The mixture was cooled to room temperature and the resulting solid was dissolved in 25 ml. hot isopropyl alcohol. The solution was cooled to room temperature, 150 ml. ether was added and the mixture was allowed to stand with cooling to 5° C. for 16 hours. The solid was collected by filtration to give after recrystallization from isopropyl alcohol-ether 10 g. 2-imino-1-(4-chlorophenyl)pyrrolidine hydrochloride; m.p. 268°-270° C.

C. The 4-chloro-N-methylaniline used above was prepared as follows:

The temperature of a mixture of 53.6 g. 4-chloroaniline, 79.5 g. methylorthoformate and 2 g. concentrated sulfuric acid, charged into a flask fitted with a fractionating column, was raised at a rate which allowed the gradual distillation of the methanol formed until a bath temperature of 175°-180° C. was reached and the reaction was held at this temperature for 30 minutes. After cooling, the mixture was distilled under reduced pressure [b.p. 141°-143° C. (9 mm.)] to give 47 g. 4-chlorophenyl-N-methylformamide as an oil which slowly solidified to a white solid. This was added to 150 ml. 10% aqueous hydrochloric acid and the mixture heated at reflux for 1 hour. The solution was chilled and treated with 15% aqueous sodium hydroxide solution until alkaline and extracted with ether. The ether extract was washed with water, dried over sodium sulfate and evaporated to dryness to give after distillation under reduced pressure 35.5 g. 4-chloro-N-methylaniline; b.p. 102°-104° C. (9 mm.).

EXAMPLE 7

1-(4-Chlorophenyl)-3,4,5,6-tetrahydro-6-phenyl-2-pyridyl)urea

A. A stirred mixture, prepared by reacting 4.1 g. sodium with 225 ml. dry acetone at room temperature, was cooled in an ice bath to 0° C. and 37.6 g. 2-amino-6-phenyl-3,4,5,6-tetrahydropyridine hydrochloride was added in one portion and stirring was continued 20 minutes. A solution of 27.4 g. 4-chlorophenyl isocyanate in 255 ml. dry acetone was then added dropwise during ½ hours with continued cooling, the ice bath was removed and stirring was continued for 2 hours. The resulting solid was collected by filtration and washed with water to give after charcoal treatment and recrystallization from acetone 31.4 g. 1-(4-chlorophenyl)-3-(3,4,5,6-tetrahydro-6-phenyl-2-pyridyl)urea; m.p. 175°-176° C.

B. The 2-amino-6-phenyl-3,4,5,6-tetrahydropyridine hydrochloride used above was prepared as follows:

To a stirred solution of 24.6 g. 2-ethoxy-6-phenyl-3,4,5,6-tetrahydropyridine in 225 ml. absolute methyl alcohol was added 6.48 g. ammonium chloride at room temperature and stirring was continued for 16 hours. The solution was evaporated to dryness under reduced pressure to give after recrystallization from isopropyl alcohol 18.1 g. 2-amino-6-phenyl-3,4,5,6-tetrahydropyridine hydrochloride; m.p. 169°-171° C. This compound also was found to possess anti-hookworm activity when tested in one dog at 100 mg./kg. (calculated on the basis of the free base) according to the procedure described hereinbefoe.

C. The 2-ethoxy-6-phenyl-3,4,5,6-tetrahydropyridine used above was prepared as follows:

To a solution of 75 g. boron trifluoride-etherate in 480 ml. anhydrous ether was added 41 g. epichlorohydrin with stirring and at a rate which maintained gentle reflux. The mixture was stirred at room temperature for 3 hours and the supernatant ether was decanted from the solid triethyloxonium fluoroborate which was then washed several times with anhydrous ether and suspended in 150 ml. methylene dichloride. A solution of 59 g. 6-phenyl-2-piperidone in 300 ml. methylene dichloride was added dropwise and the solution was stirred at room temperature for 16 hours. A 50 percent aqueous potassium carbonate solution (59.2 g.) was added with stirring and the supernatant liquid was separated from the resulting solids by decantation and evaporated to dryness under reduced pressure. The residue was distilled under reduced pressure to give 56.3 g. 2-ethoxy-6-phenyl-3,4,5,6-tetrahydropyridine; b.p. 85°-92° C. (0.04-0.2 mm.).

D. The 6-phenyl-2-piperidone used above was prepared as follows:

To 178 g. ammonium carbonate was added, during onehalf hour, 188 g. eighty-five percent formic acid and the mixture was cautiously heated to 165° C. during a 3 hour period during which time water and some formic acid were removed by distillation through an 85 cm. Vigreux column. Heating was continued for ½ hours at 165° C. after which 92 g. 4-benzoylbutyric acid was added and heating was continued for 20 hours. The mixture was cooled to room temperature, ethyl acetate was added with stirring, and the solid was collected by filtration to give after charcoal treatment and recrystallization from acetonitrile 41 g. 6-phenyl-2-piperidone; m.p. 139°-141° C.

E. The 4-benzoylbutyric acid used above was prepared as follows:

To a stirred mixture of 200 g. aluminum chloride in 200 ml. benzene, cooled to 10° C., was added portionwise (10-20 ml. portions) a solution of 75.5 g. glutaric anhydride in 200 ml. benzene during 1 hour while the temperature was maintained at about 15° C. The resulting mixture was cautiously added in portions to a mixture of 300 g. ice and 100 ml. concentrated hydrochloric acid with stirring and ice bath cooling during which the temperature rose to 60° C. The mixture was steam distilled to remove the benzene, the residue was chilled and the resulting solid was filtered and added slowly to a solution of 80 g. sodium carbonate in 500 ml. water at 80° C. The resulting solution was refluxed 15 minutes, filtered hot, and acidified at 50°-60° C. by dropwise addition of 130 ml. concentrated hydrochloric acid. The resulting mixture was chilled, filtered, washed with water and dried to give 92 g. 4-benzoylbutyric acid; m.p. 127°-129° C.

I claim:
1. 1-(4-Chlorophenyl)-3-(3,4,5,6-tetrahydro-2H-azepin-7-yl)urea or pharmaceutically acceptable acid-addition salts thereof.
2. 1-(4-Chlorophenyl)-3-(3,4,5,6-tetrahydro-2H-azepin-7-yl)urea according to claim 1.

UNITED STATES PATENT AND TRADEMARK OFFICE
CERTIFICATE OF CORRECTION

PATENT NO. : 4,052,382
DATED : October 4, 1977
INVENTOR(S) : Guy D. Diana

It is certified that error appears in the above-identified patent and that said Letters Patent are hereby corrected as shown below:

Column 3, line 34, "IV" should read -- VI --.

Column 5, line 23, "stubstance" should read -- substance --.

Column 5, line 29, "ay" should read -- any --.

Column 7, line 5, "along" should read -- alone --.

Column 7, line 30, "valves" should read -- values --.

Column 7, lines 30-31, "respentative" should read -- representative --.

Signed and Sealed this

Twenty-third Day of January 1979

[SEAL]

Attest:

RUTH C. MASON
Attesting Officer

DONALD W. BANNER
Commissioner of Patents and Trademarks